United States Patent [19]

Frey et al.

[11] Patent Number: 4,825,005
[45] Date of Patent: Apr. 25, 1989

[54] PROCESS FOR THE PREPARATION OF AROMATIC ETHER AND THIOETHER COMPOUNDS

[75] Inventors: Christian Frey, Muttenz, Switzerland; Bernd Dill, Rheinfelden, Fed. Rep. of Germany

[73] Assignee: Ciba-Geigy Corporation, Ardsley, N.Y.

[21] Appl. No.: 88,740

[22] Filed: Aug. 24, 1987

[30] Foreign Application Priority Data

Aug. 29, 1986 [CH] Switzerland ............. 3480/86

[51] Int. Cl.$^4$ .......................................... C07C 43/02
[52] U.S. Cl. ................... 568/657; 568/626; 568/635
[58] Field of Search .............. 568/657, 626, 635

[56] References Cited

U.S. PATENT DOCUMENTS 1,469,709 10/1923 Wuyts ............................ 568/657
1,941,108 12/1929 Reppe ............................ 568/657
1,959,927 10/1931 Reppe ............................ 568/626

FOREIGN PATENT DOCUMENTS 59-227836 12/1984 Japan .

OTHER PUBLICATIONS

"Synthetic Methods of Organic Chemistry", vol. 9, No. 692.
"Synthetic Methods of Organic Chemistry", vol. 13, No. 293.
"Synthetic Methods of Organic Chemistry", vol. 14, No. 280.
"Synthetic Methods of Organic Chemistry", vol. 23, No. 232.
"Synthetic Methods of Organic Chemistry", vol. 26, No. 200.

Primary Examiner—Richard L. Raymond
Assistant Examiner—Raymond Covington
Attorney, Agent, or Firm—Kevin T. Mansfield; Edward McC. Roberts

[57] ABSTRACT

The invention relates to a novel process for the preparation of ether and thioether compounds of formula

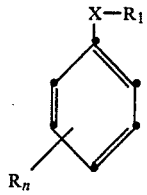

by reacting compounds of formula

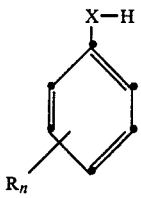

with compounds of formula $R_1-Y$ wherein R, $R_1$, X, Y and n are as defined in claim 1, in the presence of an acid acceptor and in an aliphatic ketone, which process is carried out under pressure in the temperature range from 115° to 200° C.

7 Claims, No Drawings

PROCESS FOR THE PREPARATION OF AROMATIC ETHER AND THIOETHER COMPOUNDS

The present invention relates to a novel process for the preparation of aromatic ether and thioether compounds.

According to Japanese Patent Kokai No. Sho 59-22 78 36, these compounds can be obtained from a phenol and thiophenol respectively, in the presence of a carbonate and methyl isobutyl ketone, and also from an alkyl halide under reflux conditions. When reproducing this process, however, it has been found that the conversion is unsatisfactory under the cited conditions. In particular, reference is made to the reaction of ethyl bromide with 3-diethylaminophenol in accordance with Japanese Patent Kokai No. Sho 59-22 78 36, in which a fairly large amount of starting material remains unconverted. It is therefore evident that this process is not readily applicable to all possible alkylating agents.

It has now been found that the scope of the process disclosed in Japanese Patent Kokai No. Sho 59-22 78 36 can be substantially broadened by carrying out the reaction in the temperature range from 115° to 200° C., preferably from 120° to 150° C., and under pressure. This procedure utilises on the one hand the advantageous pressure-dependent solubility even of low molecular weight readily volatile alkyl halides such as ethyl chloride or methyl bromide in the liquid ketone phase, and, on the other hand, the pressure-induced displacement of the equilibrium of the system alkali metal carbonate/water/$CO_2$/bicarbonate towards the bicarbonate. As neither water nor $CO_2$ must be expelled from the system, there is no loss of alkyl halide escaping in vapour form-a factor of great importance for an environmentally safe method of production from the ecological and economic aspect. A substantial saving of energy is also possible by the avoidance of reflux temperatures. Surprisingly, despite the use of temperatures which may be far in excess of the boiling point of the solvent and, in some cases, of that of the alkyl halide, it is possible to limit the sum of the partial pressures of $CO_2$, solvent and alkyl halide in the gas phase to the range from 0.5 to 10 bar overpressure. This is of great technical and economic importance, because normal stirred pressure reactors can be used instead of expensive autoclaves. A further advantage of this mode of operation is that metering devices for the addition of the alkyl halide can be dispensed with. The reactor can be charged at room temperature.

It has also been found that the process of this invention is not only limited to alkyl halides, but is also applicable to aryl halides, especially those of the anthraquinone series. The preparation of 1,8-diphenoxyanthraquinone from 1,8-dichloroanthraquinone may be cited by way of example.

Accordingly, the present invention relates to a process for the preparation of aromatic ether and thioether compounds of formula I

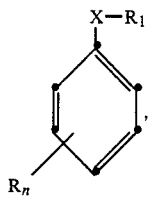
(I)

by reacting compounds of formula II

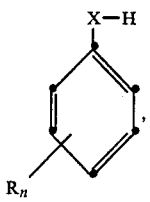
(II)

with compounds of formula III $R_1-Y$ (III)

wherein
R is a substituent,
n is 0, 1 or 2,
X is oxygen, sulfur or $-SO_2-$,
$R_1$ is unsubstituted or substituted alkyl, unsubstituted or substituted alkenyl, or aryl (e.g. phenyl, naphthyl or anthraquinoyl), and
Y is a halogen atom (e.g. chlorine, bromine or iodine), of which one or more may be present,
in the presence of an acid acceptor and in an aliphatic ketone as solvent, which process is carried out under pressure in the temperature range from 115° to 200° C.

The ether and thioether compounds of formula I are useful intermediates, especially for basic dyes.

The preferred temperature range is from 120° to 150° C., with the most preferred range being from 140° to 145° C. The pressure is from 0.5 to 10.0 bar, preferably from 0.5 to 2.0 bar, and depends on the aliphatic ketone employed and on the alkylating agent of formula III.

Suitable acid acceptors are in particular inorganic basic salts, e.g. the oxides, hydroxides, bicarbonates and carbonates of alkali metals and alkaline earth metals. Typical examples are: lithium hydroxide, sodium hydroxide, potassium hydroxide, calcium hydroxide, barium hydroxide, magnesium oxide, lithium bicarbonate, sodium bicarbonate, potassium bicarbonate, calcium bicarbonate, barium bicarbonate, lithium carbonate, sodium carbonate, potassium carbonate, calcium carbonate and barium carbonate.

A suitable solvent is an aliphatic ketone or a mixture of such ketones. The ketone is preferably one of formula IV

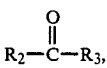
(IV)

wherein $R_2$ and $R_3$ are each independently of the other $C_1-C_4$alkyl. Typical examples of such ketones suitable for use in the process of this invention are: methyl ethyl ketone, diisopropyl ketone and methyl isobutyl ketone.

R in the compound of formula I is any substituent that does not interfere with the reaction course, e.g. a halogen atom (e.g. fluorine, chlorine or bromine), carboxyl, alkoxycarbonyl such as methoxycarbonyl, ethoxycarbonyl, allyloxycarbonyl and alkenyloxycarbonyl; $C_1$-$C_4$alkyl; heterocyclic-substituted alkyl such as pyrrolidone-substituted methyl and propyl; acyl such as acetyl; $NO_2$; dialkyl($C_1$-$C_4$)amino such as dimethylamino and diethylamino.

Possible substituents $R_1$ are the same as defined above for R. By $C_1$-$C_6$alkyl is meant e.g. methyl, ethyl, propyl, isopropyl, butyl, isobutyl, pentyl, isopentyl and hexyl. Exemplary of $C_1$-$C_6$alkenyl are: 2-allyl, 2-butenyl, 3-butenyl and 4-butenyl.

If more than one substituent Y is present in the compound of formula III, it will be readily understood that also more than one radical of the compound II of formula

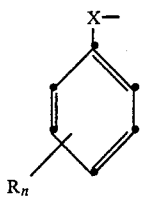

may be present in the final product of the compound of formula I.

A further advantage of the process of this invention resides in the feature that the halide of the alkali metal or alkaline earth metal formed after the process can be separated by simple filtration or washing out. It is to be particularly pointed out that alkali metal bromides (e.g. potassium bromide) can be isolated in this manner to regenerate bromine in solid form. The release of bromide ions into the wastewater is thereby avoided. The following Examples illustrate the invention.

EXAMPLE 1

A 1 liter reactor is charged with 300 ml of methyl isobutyl ketone and then 73.1 g of 3-diethylaminophenol and 153.3 g of ground potassium carbonate are added and the mixture is stirred for 30 minutes. Then 72.7 g of ethyl bromide are introduced into the autoclave, which is then closed. After heating for 3 hours to 115°–150° C. and subsequently for 5 hours at 140°–142° C. (pressure: 5 bar), the contents of the autoclave are cooled to c. 25° C. and, after addition of water, the reaction product of formula

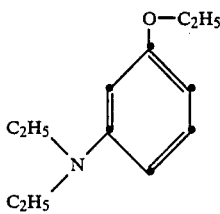

is isolated with the organic phase, which is washed with water. The solvent is removed by evaporation to give 80.9 g (yield: 97.5%) of a 96.3% product.

EXAMPLE 2

A 1 liter reactor is charged with 300 ml of methyl isobutyl ketone, 73.1 g of 3-diethylaminophenol and 153.3 g of ground potassium carbonate and the mixture is stirred for 30 minutes. Then 72.7 g of ethyl bromide are introduced into the autoclave, which is then closed and heated for 3 hours to 115°–120° C. The temperature is then kept for a further 5 hours at 140°–142° C. (pressure: 5 bar). The contents of the autoclave are cooled to c. 25° C. and potassium bromide is removed by filtration. After washing with a small amount of methyl isobutyl ketone, the combined filtrates are concentrated by evaporation, to give 75.6 g (91.1% yield) of 3-diethylaminophenetol with a titre of 96.9%.

EXAMPLE 3

A 1 liter reactor is charged with 150 ml of methyl isobutyl ketone, 73.1 g of 3-diethylaminophenol and 153.3 g of ground potassium carbonate. The mixture is stirred for 30 minutes, then 72.7 g of ethyl bromide are added and the autoclave is closed. The reaction mixture is heated first for 3 hours to 115°–129° C. and then for a further 5 hours at 140°–142° C. (pressure: 4 bar). After cooling to c. 25° C. and addition of water, the product is isolated with the organic phase, which is washed with water and concentrated by evaporation, to give 80.67 g (97.2% yield) of 3-diethylaminophenetol with a titre of 94.8%.

EXAMPLE 4

A 1 liter reactor is charged with 300 ml of methyl isobutyl ketone, 79.17 g of 2,4-dinitrophenol (100%) and 175.9 g of ground potassium carbonate and 63.6 g of methyl bromide. The autoclave is closed and heated for 3 hours to 115°–120° C. (pressure: 3.5 bar). The temperature is then kept for a further 5 hours at 140°–142° C. (pressure: 5–3 bar, falling). After cooling to c. 25° C., the solvent is distilled off at 50° C. under a partial vacuum and the salt-containing residue is taken up in warm water. 2,4-Dinitroanisole is isolated by filtration and washed with 1% ammonia solution and with warm water of c. 50° C. and dried at 50° C. under vacuum, to give 84.6 g (91.2% yield) of 2,4-dinitroanisole with a titre of 91.8%.

EXAMPLE 5

A stirred pressure reactor is charged with 183 ml of diisobutyl ketone. With stirring, 86.3 g of phenol (90%) are added. Then 103.8 g of 1,8-dichloroanthraquinone are added over 5 minutes and the reaction mixture is heated to boiling point. Distillation of water commences at 155° C. After 1.5 hours at this temperature, the reaction mixture is cooled to 35° C. and then 67 g of potassium carbonate are added. The batch is then heated to 160° C. over 90 minutes and allowed to react at this temperature for 1 hour. The reactor is then closed, heated to 175°–176° C. and kept at this temperature for 5 hours. After cooling to 30° C., the pressure in the reactor is reduced and the solvent is removed by distillation. To the reaction mixture are added 3 ml of 50% sodium hydroxide solution and the resultant 1,8-diphenoxyanthraquinone is isolated by filtration and vacuum dried, to give 141.0 g of a product with a titre of 86.2%, corresponding to a yield of 89.0%. The conversion is 99.9%.

EXAMPLE 6

In a stirred pressure reactor, 224.4 g of 3-diethylaminophenol, 64.4 g of sodium hydroxide and 20.4 g of sodium carbonate are added to 340 g of methyl isobutyl ketone. The reactor is closed and after introducing 134.4 g of ethyl chloride under pressure, the reaction mixture is heated for 3 hours to 115° C. and then for a further hour to 140° C. The reaction mixture is kept at this temperature for 10 hours. The pressure at the conclusion of the reaction has risen to about 5 bar. After cooling to 25° C., the pressure in the reactor is reduced, the contents of the reactor are rinsed with water, and the organic phase is separated from the aqueous phase. After removal of the solvent, 268 g of 3-diethylaminophenetol are isolated from the organic phase, corresponding to a yield of 97.1% and a conversion of 99.8%.

EXAMPLE 7

A reactor is charged with 360 parts of methyl isobutyl ketone and 132.7 parts of the sodium salt of 4-chlorobenzenesulfinic acid (100%) (0.665 mole; as free acid, calculated as 176.6M). The mixture is heated to the boil, with stirring, and water is removed as an azeotrope through a separator. The batch is then cooled to 25° C. and to the resultant suspension are added 115.9 parts of ground potassium carbonate (0.83 mole) and 108.7 parts of ethyl bromide (0.988 mole).

This mixture is then heated in a closed reactor for 3 hours to 115°–120° C. and heated to 140°–142° C. over 1 hour. The temperature is kept for a further 5 hours at 140°–142° C. (pressure: 3 bar). The reaction mass is cooled to 25° C., then 200 parts of water of 50° C. are added and the batch is stirred and the phases are separated. Evaporation of the organic phase affords 95 parts of 4-chlorophenylethylsulfone (89.3% of theory).

What is claimed is:

1. A process for the preparation of an aromatic ether or thioether compound of formula I

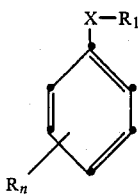 (I)

by reacting a compound of formula

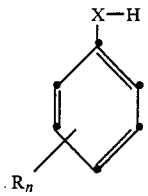 (II)

with a compound of formula

R$_1$—Y (III)

wherein
R is a non-interfering substituent,
n is 0, 1 or 2,
X is oxygen, sulfur or —SO$_2$,
R$_1$ is alkyl having 1 to 6 carbon atoms which is unsubstituted or substituted by pyrrolidine, alkenyl having 1 to 6 carbon atoms, phenyl, naphthyl or anthraquinoyl and
Y is a halogen atom,
in the presence of an acid acceptor and in an aliphatic ketone as solvent, which process is carried out at a pressure of 0.5 to 10 bar in the temperature range from 115° to 200° C.

2. A process according to claim 1, wherein the reaction temperature is in the range from 120° to 150° C.

3. A process according to claim 1, wherein the aliphatic ketone is one of formula

 (IV)

wherein R$_2$ and R$_3$ are each independently of the other C$_1$–C$_4$alkyl.

4. A process according to claim 3, wherein the aliphatic ketone is methyl ethyl ketone, diisopropyl ketone or methyl isobutyl ketone.

5. A process according to claim 1, wherein the reaction is carried out in the temperature range from 140° to 145° C.

6. A process according to claim 1, wherein the acid acceptor is an inorganic basic salt.

7. A process according to claim 6, wherein the inorganic basic salt is a hydroxide, bicarbonate or carbonate of an alkali metal or alkaline earth metal.

* * * * *